(12) United States Patent
Borrell

(10) Patent No.: US 10,111,449 B2
(45) Date of Patent: Oct. 30, 2018

(54) PRODUCTION PROCEDURE FOR A FUNCTIONAL FEED BASED IN ELLAGIC ACID, CIMENOL AND ALLIIN FROM VEGETABLE EXTRACTS TO BE USED AS PRONUTRIENT IN ANIMAL FEED

(71) Applicant: BIOVET, S.A., Cambrils (ES)

(72) Inventor: Jaime Valls Borrell, Tarragona (ES)

(73) Assignee: BIOVET, S.A., Cambrils (ES)

( * ) Notice: Subject to any disclaimer, the term of this patent is extended or adjusted under 35 U.S.C. 154(b) by 470 days.

(21) Appl. No.: 14/954,998

(22) Filed: Nov. 30, 2015

(65) Prior Publication Data
US 2017/0064979 A1 Mar. 9, 2017

(51) Int. Cl.
| | | |
|---|---|---|
| A61K 36/00 | (2006.01) |
| A23K 20/126 | (2016.01) |
| A61K 36/185 | (2006.01) |
| A61K 36/53 | (2006.01) |
| A61K 36/8962 | (2006.01) |
| A61K 31/366 | (2006.01) |
| A61K 31/015 | (2006.01) |
| A61K 31/198 | (2006.01) |
| A23K 20/105 | (2016.01) |
| A23K 20/142 | (2016.01) |
| A23K 40/10 | (2016.01) |
| A23K 10/30 | (2016.01) |
| A23K 20/111 | (2016.01) |
| A23K 20/121 | (2016.01) |
| A23K 20/158 | (2016.01) |
| A23K 20/28 | (2016.01) |
| A23K 50/30 | (2016.01) |

(52) U.S. Cl.
CPC .......... *A23K 20/126* (2016.05); *A23K 10/30* (2016.05); *A23K 20/105* (2016.05); *A23K 20/111* (2016.05); *A23K 20/121* (2016.05); *A23K 20/142* (2016.05); *A23K 20/158* (2016.05); *A23K 20/28* (2016.05); *A23K 40/10* (2016.05); *A23K 50/30* (2016.05); *A61K 31/015* (2013.01); *A61K 31/198* (2013.01); *A61K 31/366* (2013.01); *A61K 36/185* (2013.01); *A61K 36/53* (2013.01); *A61K 36/8962* (2013.01)

(58) Field of Classification Search
CPC ...................................... A61K 36/00
USPC ........................................ 424/725
See application file for complete search history.

(56) References Cited

FOREIGN PATENT DOCUMENTS

JP 2008239619 A * 10/2008

* cited by examiner

*Primary Examiner* — Michael V Meller
(74) *Attorney, Agent, or Firm* — Michael J. Bootcheck, LLC; Michael J. Bootcheck

(57) ABSTRACT

Obtention of aromatic compounds extracted from *Punica granatum*, *Thymus vulgaris* and *Allium sativum* and which have genome interaction capacity for regeneration of the enterocyte, and their use in the manufacture of functional additives for use in animal feed.

3 Claims, 1 Drawing Sheet

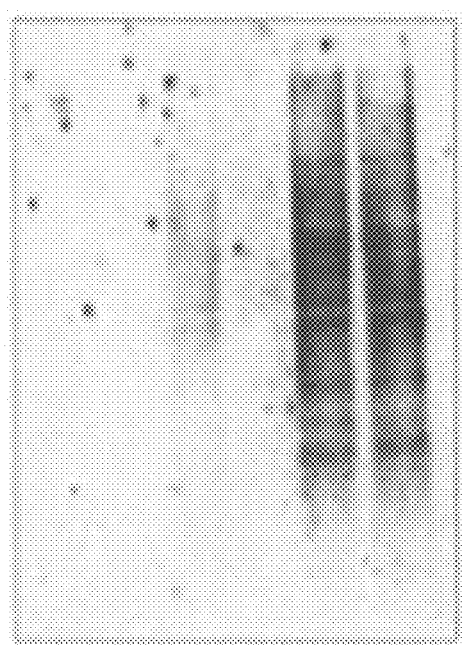

PRODUCTION PROCEDURE FOR A FUNCTIONAL FEED BASED IN ELLAGIC ACID, CIMENOL AND ALLIIN FROM VEGETABLE EXTRACTS TO BE USED AS PRONUTRIENT IN ANIMAL FEED

CROSS-REFERENCE TO RELATED APPLICATIONS

This application claims priority from co-pending Spanish Patent Application Ser. No. P201531268 filed 4 Sep. 2015, which is titled "PRODUCTION PROCEDURE FOR A FUNCTIONAL FEED BASED IN ELLAGIC ACID, CIMENOL AND ALLIIN FROM VEGETABLE EXTRACTS TO BE USED AS PRONUTRIENT IN ANIMAL FEED", which is hereby incorporated in its entirety by reference.

FIELD OF THE INVENTION

The present invention is for pronutrients for improvement of physiological state of the intestinal epithelial cells.

BACKGROUND OF THE INVENTION

The use of botanical species is widely known since antiquity.

New insights in pronutrients are allowing the study of active principles contained in plants are, what its chemical structure and which routes are followed to achieve the physiological action for which they are intended.

SUMMARY OF THE INVENTION

This invention relates to the obtention of aromatic compounds extracted from *Punica granatum, Thymus vulgaris* and *Allium sativum* and which have genome interaction capacity for regeneration of the enterocyte, and their use in the manufacture of functional additives for use in animal feed.

BRIEF DESCRIPTION OF THE FIGURES

FIG. 1 illustrates a plot of an exemplary embodiment of the present invention.

DETAILED DESCRIPTION OF THE INVENTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

First of all, *Punica granatum* will provide ellagic acid.

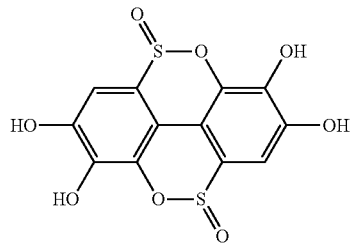 [SMILES: O=S1Oc2c(O)c(O)cc3c2-c2c1cc(O)c(O)c2OS3=O]

Ellagic acid is a polyphenol that has a complete and powerful effect on the control of free radicals that can effectively protect tissues from the effects of oxidative stress and also has antimicrobial and antiparasitic effects.

*Thymus vulgaris* extract provides cimenol, whose known functions are bactericidal, fungicidal and preservative naturally present in many botanical varieties.

The application of cimenol ring as a preservative of raw materials and feed intended for animal feed is the result of investment in R & D of Biovet S.A., together with universities, particularly with Universidad Politécnica de Valencia and with Universitat Rovira i Virgili in Tarragona.

In vitro tests and field trials indicate that cimenol ring is effective against bacteria, yeast and fungal; gastrointestinal pathogens whose mechanisms of action are:

Mechanism of Action in Bacteria

Cimenol ring in contact with bacteria causes the immediate release of cell contents into the medium, caused by the bacterial membrane perforation leading to cell destruction.

Cimenol ring inside the cell alters biosynthetic pathways affecting ATP (required for energy metabolism molecule), cellular pH and balance of inorganic ions.

Mechanism of Action in Yeast and Fungi

On yeasts and fungi, appropriate concentrations of cimenol ring achieves to kill 100% of microorganisms in just 10 minutes of contact. Cell lysis and release of cellular contents into the medium are observed. At electronic microscope, yeasts and fungi are malformed and have fractures in cell walls, especially those found in the proliferation phase.

Furthermore, cimenol ring inhibits ergosterol biosynthesis, the main sterol of yeast cell membrane, contributing to the destruction of the cell.

The underground bulb of *Allium sativum* contains numerous active components, among which sulfur compounds are shown off. If the bulb is intact and fresh, the major sulfoxide compound is S-allyl cysteine or Alliin.

This is an unstable compound which is hydrolyzed by action of the alliinase enzyme which is also present in the bulb. Allicin is obtained. Allicin is also high-volatile compound. Alliin present in the cytosol, which is also the substrate of alliinase enzyme is found in separate vacuoles. When garlic is crushed, the vacuoles containing the enzyme are broken and the reaction takes place with the alliin to form an intermediate which condenses to give allicin.

The present invention relates the production of *Allium sativum* extract to preserve intact the alliin and alliinase content so that the biochemical conversion processes Alliin in its derivatives occurs when the product enters in contact with saliva, whose conditions are suitable for activating the enzyme for hydrolysis of alliinase, so that the benefits of *Allium sativum* pronutrients are maximum, because the concentration is without losses.

This would improve the offer, with wide application in animal feed industry, based in authorized substances as feed additives.

this product have two phases. Subsequently, an extraction was made to separate the pure essential oil with a separatory funnel. The essential oil is separated in a covered and protected from light container to prevent light decomposition. A re-extraction with the aqueous portion with ether is carried out to achieve and finally separating oil surplus remaining solubilized at this stage. The remaining traces in

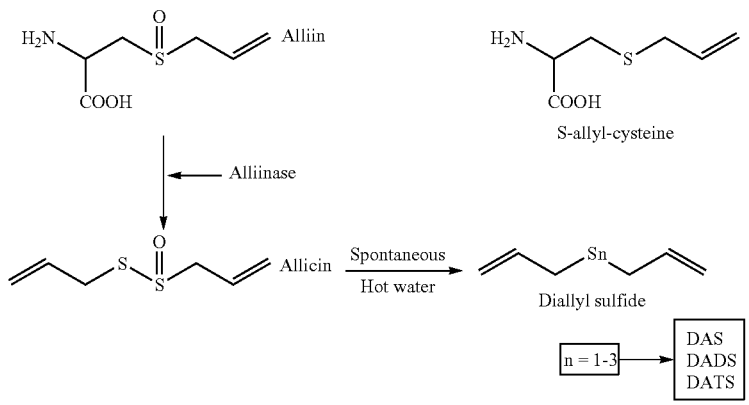

The above equation illustrates a structure of one of the major compounds in garlic and its derivatives. DAS: Diallyl sulfide; DADS: Diallyl disulfide; DATS: Diallyl trisulfide While the materials used are known, the new manufacturing process is an important step, since a product with the virtues of a product for easy storage and administration but also the nutritional content of the fresh product is obtained.

Ellagic Acid Obtained from *Punica granatum* Fruits

*Punica granatum* peels are pressed to obtain the powder portion containing ellagic acid at a concentration about 6%. This extract could be considered organic, not having any chemical treatment.

For more concentrated ellagic acid, the first organic extract is macerated in methanolic hydrochloric acid (obtained by adding 0.190 l of acetyl chloride to 98% per liter of methanol). The ratio for each kilo of pressed *Punica granatum* peel is 4 liters of methanolic hydrochloric acid. This part of the process takes place in a freezer and later the suspension is carried at 70° C. for 30 hours. After suspension in uncovered the solvents are evaporated.

Once the dry residue is obtained water is added to it and centrifuged at 6000 rpm for 30 minutes, so that the water-soluble compounds by elimination of the aqueous phase are removed.

This extraction method gets more than the double of the amount of ellagic acid (15.4%) in the extract with respect to the usual extraction methods carried out with 2 N sulphuric acid (6.1%).

Cimenol Obtaining from *Thymus Vulgaris* Leaves

To obtain ecological cimenol, dried and powdered thyme leaves are pressed in cold. The obtained cake contains about 4% cimenol.

To achieve a higher concentration of active ingredient, the above cake is put in a ball with water enough to achieve the suspension of the sample. This is usually a proportion of 1 kilo of dry thyme in 3 liters of water. The least sample handling is sought in order not to degrade the essential oils, considering that they are the primary source of the compound to be purified. Therefore, for the extraction of essential oil of thyme one steam stripping is used. Due to the volatility of oil and insolubility in water it is expected that the ether phase is extracted of water with sodium sulfate as a desiccant. To reduce the amount of components to be separated by chromatography, an acid-base extraction is performed. To obtain phenols, including cimenol, which are the most acid compounds in the essential oil, an acid-base extraction is done.

First oils in water solution are placed in the separating funnel. Then 50 ml 1N potassium hydroxide is added and as phenols are the most acidic compounds present in the oil, they are soluble in the aqueous phase. Once the aqueous phase is isolated from the rest, it is taken to a new separatory funnel for acidification with 15 ml 2N hydrochloric acid and 100 ml of ether. Thus only in phenols in ether phase are obtained. All ether phases are combined and filtered over anhydrous sodium sulfate as a desiccant to remove traces of water. Later, the compound is heated in a water bath to evaporate the ether and obtain isolated phenols. As with protease, this oil is absorbed with bentonite, which allows to get a product to a fine powder with 14-16% of cimenol. A standardization of the extract is performed to check the purity and richness of the same.

Alliin Obtained from *Allium Sativum* Bulbs

For ecological alliin, without chemical treatments, the extraction with vegetal oil is made, to avoid contact of the bulb with air to minimize the hydrolysis of the compound by the action of alliinase. The whole garlic cloves are introduced in oil and milling is done in an environment with negative pressure, in order to minimize the presence of oxygen. When finished, filtration is done to remove the peels. The product contains 5% alliin.

To increase the concentration of alliin from this emulsion an extraction will be made. For this, let stand for 2 hours and pour oily phase reducing its volume by half. Add an aqueous solution of 1 mM citric acid and treat the remaining emulsion with p-hydroxybenzoate in a ratio of 1:5 and an emulsifier and then homogenize during 30 minutes. Thus we obtain an extract of *Allium sativum* alliin at wealth of 13-14%.

Once all active substances have been purified and after checking the concentration by a quantitative analysis, the final product is prepared. This preparation takes place by simple mixing of the extracts to obtain the product in liquid form.

For preparing powdered feed supplement a first step the absorption of oily solution of *Allium sativum* extract is required. Use a bentonite particle size 74 microns to absorb the oily solution in a ratio of 5 liters per kilo of bentonite.

In this reactor 75 kilos of *Allium sativum* meal, 25 kilos of *Punica granatum* meal and 25 kilos of *Thymus vulgaris* meal are put. Time to ensure homogeneity of the product is mixed for 6 minutes. At this time, a product grinding is performed to ensure proper grading to use in industrial installations that will be the end users of the product. The complementary feed obtained by the incorporation of natural ingredients from aromatic plants, is ready to be consumed with a guaranteed 2.25% of ellagic acid, 3.5% of cimenol and 5.5% alliin minimum composition.

Properly packaged. See FIG. 1.

While the specification has been described in detail with respect to specific embodiments thereof, it will be appreciated that those skilled in the art, upon attaining an understanding of the foregoing, may readily conceive of alterations to, variations of, and equivalents to these embodiments.

The invention claimed is:

1. An animal food product consisting essentially of an extract of *Thymus vulgaris*, an extract of *Punica granatum* and an extract of *Allium sativum*, wherein the *Thymus vulgaris* has a p-cimenol content of 15%-17% by weight, the *Allium sativum* has an allin content of 20%-26% and the *Punica granatum* has an ellagic acid from 2%-4%, wherein said animal food product was treated with methanolic hydrochloric acid and wherein said product has an inductor effect on the reproduction rate of RNA-protein in swine intestinal cells.

2. An animal food product consisting essentially of an extract of *Thymus vulgaris*, an extract of *Punica granatum* and an extract of *Allium sativum*, wherein the *Thymus vulgaris* has a p-cimenol content of 15%-17% by weight, the *Allium sativum* has an allin content of 20%-26% and the *Punica granatum* has an ellagic acid from 2%-4% and wherein said animal food product has an inductor effect on the reproduction rate of RNA-protein in swine intestinal cells.

3. An animal food product consisting essentially of an extract of *Thymus vulgaris*, an extract of *Punica granatum* and an extract of *Allium sativum*, wherein the *Thymus vulgaris* has a p-cimenol content of 15%-17% by weight, the *Allium sativum* has an allin content of 20%-26% and the *Punica granatum* has an ellagic acid from 2%-4% and wherein said animal food product was treated with methanolic hydrochloric acid.

* * * * *